(12) United States Patent
Adler

(10) Patent No.: US 8,052,962 B2
(45) Date of Patent: *Nov. 8, 2011

(54) ORAL SOAP COMPOSITION FOR CLEANING TEETH

(76) Inventor: Karen A. Adler, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/709,610

(22) Filed: Feb. 22, 2007

(65) Prior Publication Data

US 2008/0206166 A1    Aug. 28, 2008

(51) Int. Cl.
*A61K 36/00* (2006.01)
*A61K 36/63* (2006.01)
*A61K 36/889* (2006.01)
*A61K 8/97* (2006.01)
*A61K 8/18* (2006.01)

(52) U.S. Cl. ............. 424/58; 424/49; 424/725; 424/727

(58) Field of Classification Search ........................ None
See application file for complete search history.

(56) References Cited

U.S. PATENT DOCUMENTS

| 2,912,385 | A | * | 11/1959 | Golub et al. | 510/138 |
| 4,525,342 | A | * | 6/1985 | Weiss et al. | 424/49 |
| 4,835,002 | A | * | 5/1989 | Wolf et al. | 426/590 |
| 7,074,391 | B1 | * | 7/2006 | Alvarez Hernandez | 424/49 |
| 2003/0236422 | A1 | * | 12/2003 | Daniels | 554/8 |
| 2004/0037790 | A1 | * | 2/2004 | Watanabe | 424/58 |
| 2006/0099153 | A1 | * | 5/2006 | Kato et al. | 424/52 |
| 2007/0173424 | A1 | * | 7/2007 | Rupert | 510/141 |

FOREIGN PATENT DOCUMENTS

| JP | 07138598 A | * | 5/1995 |
| NZ | 502158 A | * | 5/2002 |
| WO | WO 2006/079856 | * | 8/2006 |

* cited by examiner

*Primary Examiner* — Qiuwen Mi
(74) *Attorney, Agent, or Firm* — Benjamin Aaron Adler

(57) ABSTRACT

Provided herein is an oral soap composition comprising an orally-acceptable soap base effective to clean teeth that includes one or more natural oils, a saponifying agent and distilled water. The oral soap composition may be liquid or solid. Also provided are oral soap compositions comprising an essential oil for flavoring.

6 Claims, No Drawings

ORAL SOAP COMPOSITION FOR CLEANING TEETH

BACKGROUND OF THE INVENTION

1. Field of the Invention

The present invention relates to the field of dental hygiene and dental hygiene products. More specifically, the present invention relates to oral compositions comprising saponified natural oils and essential oils effective to clean teeth.

2. Description of the Related Art

Traditionally, commercial toothpastes, tooth gels and other dentifrices contain ingredients which may be harmful to an individual ingesting or otherwise improperly using them. Although specific toothpaste formulas are proprietary, the majority of them all contain one or more of certain ingredients, such as fluoride, dyes, silicates or other abrasives, sweetners, or stabilizers. There is a growing concern among the populace about the long term effects of these additives on the cost vs. benefits to oral hygiene and to the overall health of an individual. Increasingly there is a trend toward the use of natural or "green" products instead of synthetic toothpastes, tooth gels and other products associated with dental hygiene.

Thus, a recognized need is present in the art for effective oral compositions utilizing natural ingredients without synthetic additives to clean teeth. Specifically, the prior art is deficient in soaps comprising saponified oils and natural oils as cleaning agents for teeth. The present invention fulfils this longstanding need in the art.

SUMMARY OF THE INVENTION

The present invention is directed to an oral soap composition. The composition comprises an orally-acceptable soap base effective to clean teeth. The soap base may include one or more natural oils, a saponifying agent and distilled water. The present invention is directed to a related oral soap composition further comprising an essential oil effective to flavor the soap base. The present invention is directed to another related oral soap composition further comprising about 50 weight percent of filtered water whereby the soap base is liquified.

The present invention also is directed to an oral soap composition that is an orally-acceptable soap based gel effective to clean teeth. The gelled soap base may include about 14 weight percent palm oil, about 16 weight percent coconut oil, about 21 weight percent olive oil, about 12 weight percent of a saponifying agent that is potassium hydroxide, and about 35 weight percent distilled water. The present invention is directed to a related oral composition that is a liquid tooth soap further comprising about 50 weight percent of filtered water whereby the gelled soap base is liquified. The present invention is directed further to a related liquid tooth soap including an essential oil effective to flavor the liquid tooth soap that is about 0.14% to about 1.0% of a total weight thereof.

The present invention is directed further to an oral soap composition that is an orally-acceptable solid soap base effective to clean teeth. The solid soap includes about 17 weight percent palm oil, about 20 weight percent coconut oil, about 26 weight percent olive oil, about 10 weight percent of a saponifying agent that is sodium hydroxide, and about 26 weight percent distilled water. The present invention is directed to a related solid soap composition further comprising an essential oil effective to flavor the solid soap base that is about 0.3% to about 3.0% of a total weight thereof.

Other and further aspects, features, benefits, and advantages of the present invention will be apparent from the following description of the presently preferred embodiments of the invention given for the purpose of disclosure.

DETAILED DESCRIPTION OF THE INVENTION

In one embodiment of the present invention there is provided an oral soap composition, comprising an orally-acceptable soap base effective to clean teeth, including one or more natural oils; a saponifying agent; and distilled water.

Further to this embodiment the oral soap composition may comprise an amount of an essential oil effective to flavor the soap base. The essential oil may be about 0.1% to about 3% of total weight of the soap base. Examples of essential oils are peppermint, spearmint, cinnamon, ginger, orange, lime, lemon, grapefruit, clove, fennel, bergamot, thyme, lemon grass, coriander, chamomile, manuka, celery seed, rosemary, basil, eucalyptus, or oregano. In another further embodiment the oral soap composition may comprise about 70 weight percent of filtered water wherein the soap base is liquified.

In all these embodiments the natural oil may be palm oil, coconut oil or olive oil or other orally-acceptable natural oil. The palm oil may be at a weight percent of about 14 to about 18. The coconut oil may be at a weight percent of about 16 to about 20. The olive oil may be at a weight percent of about 21 to about 27. Also the saponifying agent may be potassium hydroxide or sodium hydroxide. The potassium hydroxide may be at a weight percent of about 11 to about 12. The sodium hydroxide may be at a weight percent of about 10 to about 11.

Preferably, the orally-acceptable soap base may include about 14 weight percent to about 18 weight percent palm oil; about 16 weight percent to about 20 weight percent coconut oil; about 21 weight percent to about 27 weight percent olive oil; about 10 weight percent to about 12 weight percent of a saponifying agent; and about 26 weight percent to about 36 weight percent distilled water.

In one aspect of this preferred embodiment, the soap base is a gel including about 14 weight percent palm oil, about 16 weight percent coconut oil, about 21 weight percent olive oil, about 11 weight percent of a saponifying agent that is potassium hydroxide, and about 36 weight percent distilled water. Further to this aspect the gelled soap base may comprise about 50 weight percent filtered water wherein the gelled soap base is liquified. Further still the liquid soap base may comprise an amount of an essential oil effective to flavor the liquid tooth soap that is about 1 weight percent peppermint oil, spearmint oil, cinnamon oil, ginger oil, or orange oil or about 0.3 weight percent lime oil or about 0.14 weight percent lemon oil of the liquid soap base.

In another aspect of these embodiments the soap base may be a solid including about 17 weight percent palm oil, about 20 weight percent coconut oil, about 26 weight percent olive oil, about 10 weight percent of a saponifying agent that is sodium hydroxide, and about 26 weight percent distilled water. Further to this aspect the solid soap base may comprise an amount of an essential oil effective to flavor the solid tooth soap that is about 3 weight percent peppermint oil or ginger oil or about 2 weight percent spearmint oil or orange oil or about 1 weight percent cinnamon oil or lime oil or about 0.3 weight percent lemon oil of the solid soap base.

In a related embodiment of the present invention there is provided an oral soap composition comprising an orally-acceptable soap based gel effective to clean teeth, including about 14 weight percent palm oil; about 16 weight percent coconut oil; about 21 weight percent olive oil; about 12 weight percent of a saponifying agent that is potassium hydroxide; and about 35 weight percent distilled water.

Further to this embodiment the oral soap composition may comprise an amount of filtered water effective to liquefy the gelled soap base that is about 50 weight percent of the resulting liquid tooth soap composition. In yet a further embodiment the liquid tooth soap may comprise an amount of an essential oil effective to flavor the liquid soap base that is about 0.14% to about 1.0% of a total weight thereof. Preferably, the essential oil may be about 1 weight percent peppermint oil, spearmint oil, cinnamon oil, ginger oil, or orange oil or about 0.3 weight percent lime oil or about 0.14 weight percent lemon oil of the liquid soap base.

In another related embodiment of the present invention there is provided an oral soap composition, comprising an orally-acceptable solid soap base effective to clean teeth, including about 17 weight percent palm oil; about 20 weight percent coconut oil; about 26 weight percent olive oil; about 10 weight percent of a saponifying agent that is sodium hydroxide; and about 26 weight percent distilled water.

Further to this embodiment the solid soap base may comprise an amount of an essential oil effective to flavor the solid soap base that is about 0.3% to about 3.0% of a total weight thereof. Preferably, the essential oil is about 3 weight percent peppermint oil or ginger oil or about 2 weight percent spearmint oil or orange oil or about 1 weight percent cinnamon oil or lime oil or about 0.3 weight percent lemon oil of the solid soap base.

As used herein, the term "a" or "an" when used in conjunction with the term "comprising" in the claims and/or the specification may mean "one," but it is also consistent with the meaning of "one or more," "at least one," and "one or more than one." As used herein, the term "or" in the claims is used to mean "and/or" unless explicitly indicated to refer to alternatives only or the alternatives are mutually exclusive, although the disclosure supports a definition that refers to only alternatives and "and/or."

As used herein, the terms "soap", "soap base", "gelled soap base", "oral tooth soap", "solid soap base", "liquid tooth soap", or "tooth soap" refer to a substance for cleaning teeth that comprises natural oils or fats saponified with a strong alkali and, optionally, an essential oil", as flavoring. The terms "saponify", "saponifying" or "saponification" are well known to one of ordinary skill in the art of soap making and retain their ordinary meanings within this technology.

As used herein, the term "natural oil" refers to unrefined, i.e., not distilled, plant oils that are obtained by a mechanical process.

As used herein, the term "essential oil" refers to a concentrated, hydrophobic liquid containing a volatile aromatic compound(s) from a plant that is produced by distillation.

As used herein, the term "distilled water" refers to purified water whereby minerals, e.g., calcium and magnesium, which are usually in the form of carbonates, trace elements and other impurities are removed by distillation.

As used herein, the term "filtered water" refers to drinking water whereby impurities are removed by filtration.

The present invention provides an oral composition effective as a soap for cleaning teeth. More particularly, the oral composition is a soap comprising one or more saponified natural oils, for example, palm oil, coconut oil, olive oil or other orally-acceptable natural oil, in a distilled water vehicle. Optionally, essential oils of plants, such as, but not limited to, the terpenes peppermint, spearmint, cinnamon, ginger, or citrus, e.g., orange, lime, lemon, or grapefruit are incorporated into the soap as a flavoring. In addition essential oils from clove, fennel, bergamot, thyme, lemon grass, coriander, chamomile, manuka, celery seed, rosemary, basil, eucalyptus, or oregano are useful as, for example, flavorings. The saponifying agent or alkali used to saponify the natural oils determines the resulting consistency of the soap.

Generally, the one or more natural oils comprises about 14 weight percent to about 52 weight percent of the soap base. For example, palm oil may have a weight percent of about 14 to about 18. Coconut oil may have a weight percent of about 16 to about 20. Olive oil may have a weight percent of about 21 to about 27. Preferably, the soap base includes palm oil, coconut oil and olive oil. The saponifying agent may be a strong alkali such as potassium hydroxide or sodium hydroxide. The saponifying agent may comprise about 10 weight percent to about 12 weight percent of the soap base and distilled water may comprise about 26 weight percent to about 36 weight percent. The essential oil comprises about 0.1% to about 3% of total weight of the soap base.

In one preferred form of the invention the oral composition or tooth soap may be substantially liquid in character. To obtain a final liquid composition, saponification of the natural oils is performed using the alkali potassium hydroxide (KOH) in an amount of about 11 wt % to about 12 wt % and a distilled water. The natural oils comprise the soap base in amounts of about 14 weight percent palm oil, about 16 weight percent coconut oil, about 21 weight percent olive oil and distilled water comprises about 35 weight percent. A liquid tooth soap comprises a solution of 50 wt % gelled soap base and 50 wt % filtered water. To flavor the liquid tooth soap one of the essential oils is added in an amount of about 1 weight percent peppermint oil, spearmint oil, cinnamon oil, ginger oil, or orange oil or about 0.3 weight percent lime oil or about 0.14 weight percent lemon oil.

Alternatively, in another preferred form of the invention the oral composition or tooth soap may be substantially solid in character. To obtain a final solid composition, saponification of the natural oils is performed using the alkali sodium hydroxide (NaOH) in an amount of about 10 wt % to about 11 wt %. To flavor the solid tooth soap one of the essential oils is added prior to solidification in an amount of about 3 weight percent peppermint oil or ginger oil or about 2 weight percent spearmint oil or orange oil or about 1 weight percent cinnamon oil or lime oil or about 0.3 weight percent lemon oil.

The following examples are given for the purpose of illustrating various embodiments of the invention and are not meant to limit the present invention in any fashion.

Example 1

General Materials and Methods

All components of the tooth soaps and equipment described herein are commercially available to the public. Production processes as described infra are adapted for small batches easily produced on a kitchen stovetop using standard temperature settings, such as high, medium low. It would be easily within the purview of one of ordinary skill in the art to scale the process up or down as desired. In addition one of ordinary skill would readily recognize how to correlate a stove top setting to a temperature range. Temperatures of the heated and/or melted components are monitored easily using a suitable thermometer, either analog or digital, with a temperature scale encompassing at least a 120° F. to 170° F. range or comparable centigrade range, for example, a candy thermometer or a frying oil thermometer.

Example 2

Liquid Tooth Soap

Preparation of Soap Base Gel

The required amounts of the natural oils, saponifying agent and distilled water are shown in Table 1 below. Combine the potassium hydroxide and distilled water to form a lye solution. Palm oil and coconut oil are solids at room temperature. These natural oils and the olive oil, e.g., extra virgin olive oil, are combined and melted/heated using steam heat, e.g., in a double boiler, at a high heat setting to a temperature of 170° F. Heating is discontinued and the lye solution is slowly combined with the melted/heated natural oils while whisking the resulting soap base mixture.

The soap base liquid mixture is further heated in the double boiler, for example, at medium heat with constant mixing using, alternately, a whisk and a stick blender for about 15 min. until the liquid suddenly becomes a thick paste. Continue heating the paste for 3 hrs on medium heat and stir with a spoon at 20 min intervals. The paste will become a translucent soap base gel as it cools. The gelled soap base may be stored in a refrigerator or reliquified for immediate use.

TABLE 1

| Soap base component | Weight | | |
|---|---|---|---|
| | oz | kg | wt % |
| palm oil | 34 | 0.964 | 14.57 |
| coconut oil | 38.6 | 1.09 | 16.48 |
| olive oil | 50.8 | 1.44 | 21.77 |
| potassium hydroxide | 27.5 | 0.78 | 11.79 |
| distilled water | 82.6 | 2.34 | 35.39 |
| total | | 6.614 | 100 |

Reliquifying the Gelled Tooth Soap Base

In this example gelled soap base is liquified in filtered water at 50 weight percent. Filtered water and gelled tooth soap base are combined and heated over medium heat for about 1.5 hrs until the gel is liquified. The liquid tooth soap cools for about 0.5 hrs and then poured into a container, e.g., a carboy. The liquid tooth soap stands in the container for 7 days to allow for further saponification of the natural oils and evaporation of excess potassium hydroxide resulting in clarification of the liquid.

Flavoring Liquid Tooth Soap

An essential oil as flavoring may be added to the liquid tooth soap base. In this example the weight in ounces or grams shown in Table 2 is based on 48 oz or 1.36 kg total weight of the liquid soap base. Table 2 also shows the weight percent of essential oil to total weight of liquid soap base. The appropriate amount of essential oil is mixed into the appropriate amount of liquid soap base using a whisk. The resulting flavored liquid soap base may be packaged in a suitable container, e.g., a brown glass bottle to protect it from light.

TABLE 2

| Essential oil | Weight | | wt % of total |
|---|---|---|---|
| | oz | gm | soap base wt |
| peppermint | 0.56 | 16 | 1.18 |
| spearmint | 0.56 | 16 | 1.18 |
| cinnamon | 0.42 | 12 | 0.882 |
| ginger | 0.56 | 16 | 1.18 |
| orange | 0.35 | 10 | 0.735 |

TABLE 2-continued

| Essential oil | Weight | | wt % of total |
|---|---|---|---|
| | oz | gm | soap base wt |
| lime | 0.14 | 4 | 0.294 |
| lemon | 0.07 | 2 | 0.147 |

Example 3

Solid Tooth Soap

Preparation of Tooth Soap Base

The required amounts of natural oils, saponifying agent and distilled water are shown in Table 3. Combine the sodium hydroxide and distilled water to form a lye solution. Palm oil and coconut oil are solids at room temperature and are combined and melted over low heat where the temperature of the melted oils does not exceed 120° F. The olive oil, for example, extra virgin olive oil, is added to the melted palm and coconut oils. Separately, heat the natural oils and the lye solutions to 100° F. While mixing, slowly pour the heated lye solution into the heated oils to make the soap base.

A thin film, known as "trace", will form on the surface of the soap base solution. At this stage an essential oil as flavoring may be added to the soap base solution in an amount shown in Table 4. The essential oil is added to the soap base with continuous mixing about 20 min or until the solution has cooled to a point where it is almost too thick to pour.

The flavored soap base is poured into paper-lined boxes and placed in an insulated environment to maximally increase the time required for the soap base to cool. Representative boxes may include wooden boxes or soap molds lined with freezer paper or other paper with a plastic film coating on one side. Without being limiting, the boxes containing the soap may be placed in insulated containers, such as a styrofoam container, and, optionally, further covered with insulating blankets and/or the insulated containers stored in an insulated room in which the ambient temperature may be regulated. It is contemplated that slow cooling allows any remaining free sodium hydroxide to evaporate from the soap base. After two days the soap may be cut into appropriate or desired sizes and placed on racks to cure. The soap cures for approximately four weeks and is then ready to use.

TABLE 3

| Soap base component | Weight | | |
|---|---|---|---|
| | oz | kg | wt % |
| palm oil | 34 | 0.964 | 17.49 |
| coconut oil | 38.6 | 1.09 | 19.78 |
| olive oil | 50.8 | 1.44 | 26.13 |
| sodium hydroxide | 19.6 | 0.556 | 10.10 |
| distilled water | 51.6 | 1.46 | 26.5 |
| total | | 5.51 | 100 |

TABLE 4

| Essential oil | Weight | | wt % of total |
|---|---|---|---|
| | oz | gm | soap base wt |
| peppermint | 5.0 | 142 | 2.58 |
| spearmint | 3.5 | 99 | 1.80 |

TABLE 4-continued

| Essential oil | Weight oz | Weight gm | wt % of total soap base wt |
|---|---|---|---|
| cinnamon | 2.5 | 71 | 1.29 |
| ginger | 5.0 | 142 | 2.58 |
| orange | 3.2 | 91 | 1.65 |
| lime | 1.2 | 34 | 0.617 |
| lemon | 0.6 | 17 | 0.308 |

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. An oral soap composition, consisting of:
   a) an orally-acceptable, tooth-cleaning saponified liquid soap base,
      i) olive oil at about 21 weight percent to about 27 weight percent;
      ii) palm oil at about 14 weight percent to about 18 weight percent;
      iii) coconut oil at about 16 weight percent to about 20 weight percent, said oils saponified by about 10% to about 12% weight percent of potassium hydroxide in about 26 to about 36 weight percent distilled water to form a liquefied saponified soap base; and
      iv) filtered water as liquifier; and
   b) an essential oil flavoring.

2. The oral soap composition of claim 1, wherein the essential oil is about 0.1% to about 3% of a total weight of the saponified liquid soap base.

3. The oral soap composition of claim 1, wherein the essential oil flavoring is obtained from peppermint, spearmint, cinnamon, ginger, orange, lime, lemon, grapefruit, clove, fennel, bergamot, thyme, lemon grass, coriander, chamomile, manuka, celery seed, rosemary, basil, eucalyptus, or oregano.

4. The oral soap composition of claim 1, wherein the palm oil is about 14 weight percent, the coconut oil is about 16 weight percent, the olive oil is about 21 weight percent, the potassium hydroxide is about 11 weight percent, and the distilled water is about 36 weight percent, and the essential oil is about 1 weight percent peppermint oil, spearmint oil, cinnamon oil, ginger oil, or orange oil or about 0.3 weight percent lime oil or about 0.14 weight percent lemon oil of a total weight percent of the saponified liquid soap base.

5. An oral soap composition, consisting of:
   a) an orally-acceptable, tooth-cleaning saponified liquid soap base, including:
      i) about 14 weight percent palm oil;
      ii) about 16 weight percent coconut oil;
      iii) about 21 weight percent olive oil, said oils saponified by about 12 weight percent of a potassium hydroxide in about 35 weight percent distilled water to form a liquefied saponified soap base; and
      iv) filtered water as liquifier; and
   b) an essential oil flavoring at about 0.14 weight percent to about 1.0 weight percent of the total weight of the saponified liquid soap base.

6. The oral soap composition of claim 5, wherein the essential oil flavoring is about 1 weight percent peppermint oil, spearmint oil, cinnamon oil, ginger oil, or orange oil or about 0.3 weight percent lime oil or about 0.14 weight percent lemon oil.

* * * * *